United States Patent
Pan et al.

(10) Patent No.: US 9,643,023 B2
(45) Date of Patent: May 9, 2017

(54) METHOD FOR MONITORING POWER SUPPLY TO IMPLANTABLE MEDICAL DEVICE

(71) Applicant: GiMer Medical Co., Ltd., New Taipei (TW)

(72) Inventors: Jian-Hao Pan, New Taipei (TW); Chii-Wann Lin, New Taipei (TW); Chi-Heng Chang, New Taipei (TW)

(73) Assignee: GiMer Medical Co., Ltd., New Taipei (TW)

( * ) Notice: Subject to any disclaimer, the term of this patent is extended or adjusted under 35 U.S.C. 154(b) by 0 days.

(21) Appl. No.: 14/854,549

(22) Filed: Sep. 15, 2015

(65) Prior Publication Data
US 2016/0001085 A1    Jan. 7, 2016

Related U.S. Application Data

(63) Continuation-in-part of application No. 14/166,857, filed on Jan. 29, 2014, now Pat. No. 9,399,142.

(51) Int. Cl.
| | | |
|---|---|---|
| *A61N 1/00* | (2006.01) | |
| *A61N 1/378* | (2006.01) | |
| *A61N 1/372* | (2006.01) | |

(52) U.S. Cl.
CPC ........ *A61N 1/3787* (2013.01); *A61N 1/37223* (2013.01); *A61N 1/37247* (2013.01)

(58) Field of Classification Search
USPC ...................................... 607/46, 57
See application file for complete search history.

(56) References Cited

U.S. PATENT DOCUMENTS

2005/0216070 A1* 9/2005 Boveja ............. A61N 1/08
607/46

* cited by examiner

*Primary Examiner* — Nicole F Johnson
(74) *Attorney, Agent, or Firm* — Muncy, Geissler, Olds & Lowe, P.C.

(57) ABSTRACT

An external control device includes a human-computer interface, a first controller and a power transmitting unit. An implantable medical device includes a power receiving unit, a second controller and a second detector. A method for monitoring power supply comprises: producing a first magnetic field by the power transmitting unit; sensing the first magnetic field to produce a second magnetic field and converting it into a direct current by the power receiving unit; detecting a power value of the direct current by the second detector to output a detection signal to the second controller; outputting a status information to the external control device by the second controller according to the detection signal; and receiving the status information by the first controller. The first controller transmits an adjustment signal to the power transmitting unit if informed of the status information that the power value is not within a designate power range.

13 Claims, 2 Drawing Sheets

METHOD FOR MONITORING POWER SUPPLY TO IMPLANTABLE MEDICAL DEVICE

CROSS REFERENCE TO RELATED APPLICATIONS

This application is a Continuation-In-Part of U.S. application Ser. No. 14/166,857 filed on Jan. 29, 2014, patented on Jul. 26, 2016 (U.S. Pat. No. 9,399,142 B2), the entire contents of which are hereby incorporated by reference.

BACKGROUND

Technical Field

The invention relates to a method for monitoring power supply, in particular to a method for monitoring power supply to the implantable medical device which is implantable in organism.

Related Art

Currently, through the advancement of technology, medical devices, namely implantable medical devices, have already been miniaturized so that they can be implanted inside human bodies for various treatment applications. For example, the implantable medical devices are implantable nerve stimulation devices, glucose sensors or pacemakers, etc. Because the power source is necessary for these devices, micro battery is commonly utilized as the power supply. However, the lifetime of the micro battery is not long enough, so it is not appropriate to the implantable medical device.

Due to battery lifetime, recent development has chosen to transmit power through wireless means. Although wireless power suffers inferior efficiency compared to wired power, it has other advantages of application to the implantable medical devices. In details, if the implantable medical device is equipped with wireless power, the patient may get rid of the risk of battery failure or be relieved from suffering another surgery due to battery exhaustion. Furthermore, wireless power also enhances the operation lifetime of the implantable medical device.

Recently, wireless power technique such as resonant inductive coupling is generally employed in the wireless transmission of electrical power. The transmission end and the reception end all have LC resonance mechanisms so that the transmission end is easier in producing high-power time-varying current, corresponding magnetic fluxes are induced on the inductive coils, and the reception end is easier in obtaining the transmitted energy.

When wireless power technique is applied to the implantable medical device, usually the reception coil has to be aligned with the transmission coil in an external control device so as to obtain the highest amount of energy. If the transmission and reception coils are perpendicular, a less amount of energy is received and the implantable medical device may not be able to function. Thus, the depth or position or other factor of the implantable medical device inside the organism also affects alignment and it may cause poor efficiency of wireless power. Besides, the implantable medical device may obtain different amounts of power due to the distance and alignment between the transmission and reception coils. If the received power is too high, the temperature of the implantable medical device rises and it may even exceed the maximum voltage limitation of the implantable medical device and cause the circuit broken. If the received power is too low, the implantable medical device is not able to operate due to lack of sufficient supplied power.

Therefore, a method for monitoring power supply to the implantable medical device implanted inside the organism particularly inside the patient is expected to monitor the power supply status and timely effectively adjust the transmission power for optimized performance during wirelessly powered by an external control device.

SUMMARY

One aspect of the disclosure is to provide a method for monitoring power supply to the implantable medical device implanted inside the organism particularly inside the patient to monitor the power supply status and timely effectively adjust the transmission power for optimized performance during wirelessly powered by an external control device.

A method for monitoring power supply to an implantable medical device interacting with an external control device is provided. The external control device includes a human-computer interface, a first controller and a power transmitting unit, and the implantable medical device includes a power receiving unit, a second controller and a second detector. The method comprises: producing a first magnetic field by the power transmitting unit; sensing the first magnetic field to produce a second magnetic field and converting the second magnetic field into a direct current by the power receiving unit; detecting a power value of the direct current by the second detector to output a first detection signal to the second controller; outputting a first status information to the external control device by the second controller according to the first detection signal; and receiving the first status information by the first controller. The first controller transmits an adjustment signal to the power transmitting unit if informed of the first status information that the power value is not within a designate power range.

In one embodiment, the first controller directs the power transmitting unit to produce the first magnetic field according to a parameter indication signal inputted from the human-computer interface.

In one embodiment, the designate power range is between 0.5 W and 2 W.

In one embodiment, after received by the first controller, the first status information is displayed on the human-computer interface.

In one embodiment, if informed of the first status information that the power value is not within the designate power range, the first controller is instructed from the user input on the human-computer interface to transmit the adjustment signal to the power transmitting unit.

In one embodiment, the designate power range is between 0.5 W and 2 W.

In one embodiment, the adjustment signal is adapted to adjust the output power of the power transmitting unit for restricting the power value within the designate power range.

In one embodiment, the designate power range is between 0.5 W and 2 W.

In one embodiment, the method further comprises: detecting the temperature and the power dissipation of the power transmitting unit by a first detector of the external control device.

In one embodiment, the implantable medical device further comprises a sensing unit electrically connected to the second controller.

In one embodiment, the method further comprises: sensing a temperature value of the implantable medical device by the sensing unit to output a sensing signal to the second controller; outputting a second status information to the external control device by the second controller according to the sensing signal; and displaying the temperature value on the human-computer interface by the first controller according to the second status information.

In one embodiment, the implantable medical device further comprises a function circuit electrically connected to the second controller.

In one embodiment, the method further comprises: transmitting an operated treatment data to the second controller by the function circuit; outputting a third status information to the external control device by the second controller according to the treatment data; and displaying the treatment data on the human-computer interface by the first controller according to the third status information.

In one embodiment, the external control device and the implantable medical device respectively further comprises a first signal transceiver unit and a second signal transceiver unit, the second controller outputs the first status information to the first signal transceiver unit by the second signal transceiver unit.

The detector of the implantable medical device may immediately detect the power value outputted by the power receiving unit, and report the detected status to the external control device by wireless transmission. Thus, the external control device can timely adjust the output power of the power amplifier. The implantable medical device, when wirelessly powered, is not greatly affected by the depth or alignment of implantation. A desired treatment effect is as such achieved, in addition to convenient user operation.

BRIEF DESCRIPTION OF THE DRAWINGS

The embodiments will become more fully understood from the detailed description and accompanying drawings, which are given for illustration only, and thus are not limitative of the present invention, and wherein.

DETAILED DESCRIPTION OF THE INVENTION

The embodiments of the invention will be apparent from the following detailed description, which proceeds with reference to the accompanying drawings, wherein the same references relate to the same elements.

The implantable medical device may be an electronic device for medical treatment which can be implanted in the organism. It may be for example but not limited to an implantable nerve stimulator, a blood glucose sensor or an artificial pacemaker. The method for monitoring power supply in the disclosure is not limited to the field of medical treatment. For the sake of clarity, in the following description, a nerve stimulation device is taken as the implantable medical device and applied to treatment or relief of an organism's pain for example. Furthermore, the organism may include mammal such as mouse, human, rabbit, cattle, sheep, pig, monkey, dog, cat, etc. Preferably, it is human.

Figure 1:
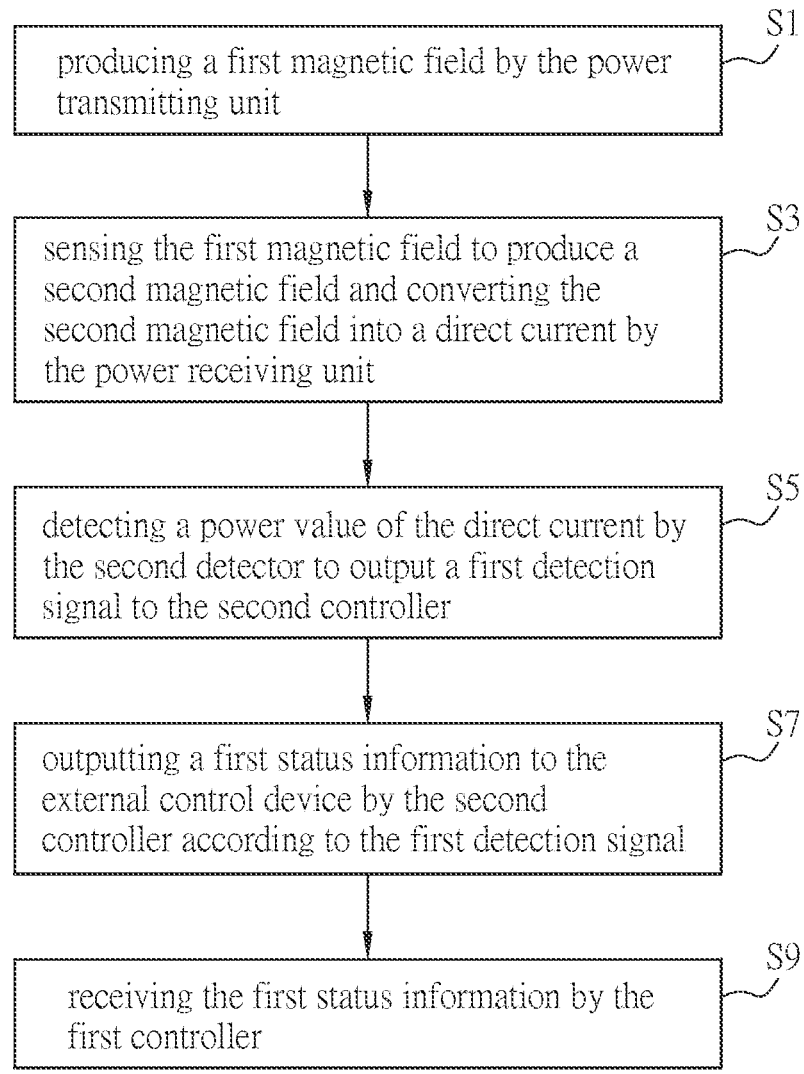
FIG. 1 is a flow chart showing the steps of the method for monitoring power supply to the implantable medical device according to the embodiment.

FIG. 1 is a flow chart showing the steps of the method for monitoring power supply to the implantable medical device according to the embodiment. Referring to FIG. 1, in the embodiment, the method for monitoring power supply includes steps of: producing a first magnetic field by the power transmitting unit (S1); sensing the first magnetic field to produce a second magnetic field and converting the second magnetic field into a direct current by the power receiving unit (S3); detecting a power value of the direct current by the second detector to output a first detection signal to the second controller (S5); outputting a first status information to the external control device by the second controller according to the first detection signal (S7); and receiving the first status information by the first controller (S9). The first controller transmits an adjustment signal to the power transmitting unit if informed of the first status information that the power value is not within a designate power range.

For the sake of clarity regarding the step details of the method, the circuits and interaction of the implantable medical device and the external control device are explained first in the following paragraphs. Then, the following paragraphs describe the method for monitoring power supply which interacts with and is applied to the implantable medical device and the external control device. However, the descriptions in the following embodiments are exemplary but not intended to limit the scope of the invention.

Figure 2:
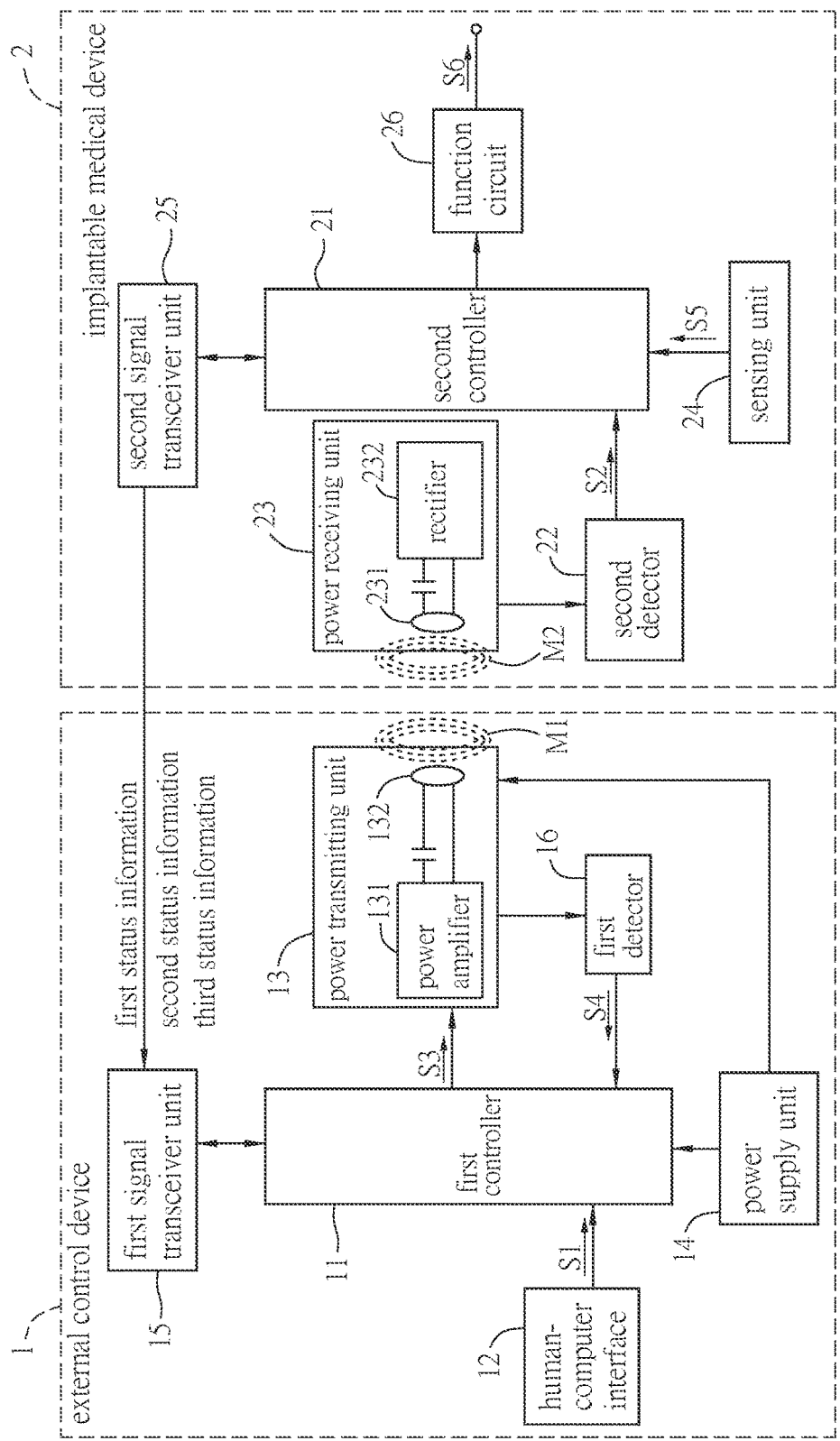
FIG. 2 is a block diagram showing the implantable medical device and the external control device.

Referring to FIG. 2, it is a block diagram showing the implantable medical device and the external control device. In the embodiment, the implantable medical device 2 is implantable into a human body, and it is wirelessly powered by an external control device 1. Elements of the implantable medical device 2 and the external control device 1 and their relationships will be described in the following paragraphs.

In the embodiment, the external control device 1 includes a first controller 11, a human-computer interface 12, a power transmitting unit 13 and a power supply unit 14. The human-computer interface 12 and the power transmitting unit 13 are respectively coupled to the first controller 11. The power supply unit 14 is coupled to the first controller 11 and the power transmitting unit 13, and it acts as the power source of the external control device 1. The power supply unit 14 may be a battery or a rechargeable battery, or it may be a power adapter connected to mains electricity to supply electrical power. The implantable medical device 2 includes a second controller 21, a second detector 22 and a power receiving unit 23. The second detector 22 and the power receiving unit 23 are respectively coupled to the second controller 21.

In the embodiment, before step S11, the user may use the human-computer interface 12 of the external control device 1 to initialize the system default values of the external control device 1. He may also use the human-computer interface 12 to input the required configuration parameters with a parameter indication signal S1 to the first controller 11. In the embodiment, the human-computer interface 12 may be for example but not limited to touch button, touch panel, physical button or their combination.

The first controller 11 and the second controller 21 may be implemented with digital circuit such as IC or implemented with analog circuit. For example, IC may be a microprocessor, a MCU, a programmable logic gate array (for example FPGA or CPLD) or ASIC. In the embodiment, it is a MCU for example but not limited thereto.

In the embodiment, the power transmitting unit 13 includes a power amplifier 131 and a first coil 132. When the first controller 11 receives inputted parameters from the parameter indication signal S1 of the human-computer interface 12, it correspondingly set an operation frequency of the power amplifier 131 according to the inputted parameters. As a result, the power amplifier 131 begins to operate according to an initial power. For example, the second coil 231 of the implantable medical device 2 may be a series LC resonator, and the first coil 132 of the external control device 1 may similarly be a series LC resonator, too. Both they have identical resonant frequency which is for example but not limited to the formula:

$$f_r = 1/(2\pi (L_S C_S)^{1/2}).$$

The external control device 1 drives the first coil 132 into LC resonance through the power amplifier 131. In the embodiment, the power amplifier 131 is a class D power amplifier, and the operation frequency of the power amplifier 131 is controlled by the first controller 11. In step S11 of the embodiment, the time-varying current on the first coil 132 accordingly produces magnetic flux so that the first coil 132 correspondingly produces a first magnetic field M1. As the operation frequency is closer to the resonant frequency, the first coil 132 produces greater current and the transmission power is also greater.

The power receiving unit 23 includes a second coil 231 and a rectifier 232. In step S13, the power receiving unit 23 senses the first magnetic field M1 to produce a second magnetic field M2, and converts the second magnetic field M2 into a direct current. For example, after the second coil 231 senses an AC electromagnetic field and correspondingly resonate to output an alternating current, the rectifier 232 rectifies the alternating current to a direct current. The direct current can be supplied to the elements of the implantable medical device 2 to operate.

For example, according to the parameters stored in the memory, the first controller 11 may voluntarily direct the power transmitting unit 13 to produce the first magnetic field M1. Thus, it is not necessary for the user to input through the human-computer interface 12.

For effectively monitoring the power supply efficiency, in step S15, the second detector 22 of the implantable medical device 2 is electrically connected to the rectifier 232 of the power receiving unit 23. The second detector 22 detects a power value of the direct current to output a first detection signal S2 to the second controller 21. For example, the method of detecting the power value may include measuring the voltage of the direct current and the current flowing into the implantable medical device 2 at the same time and then obtaining the power value of the direct current by computing the above parameters. The implantable medical device 1 further includes a second signal transceiver unit 113 coupled to the second controller 21. In step S17, according to the first detection signal S2, the second controller 21 directs the second signal transceiver unit 25 to transmit a first status information to a first signal transceiver unit 15 of the external control device 1 by wireless transmission. Then in step S19, the first signal transceiver unit 15 transmits the first status information to the first controller 11, so the first controller 11 of the external control device 1 also receives the status information about the power value of the implantable medical device 2, and the human-computer interface 12 of the external control device 1 is updated to display the status information about the implantable medical device 2. For example, if informed of the first status information that the power value is not within a designate power range, the first controller 11 transmits an adjustment signal S3 to the power transmitting unit 13.

However, the above implementation of displaying the first status information on the external control device 1 is not limited. In other embodiments, for example, if informed of the first status information that the power value is not within the designate power range, the user may use the human-computer interface so the first controller is instructed from the user input on the human-computer interface to transmit the adjustment signal to the power transmitting unit, but it is not limited thereto. In other words, the first controller may voluntarily (decide by itself) or passively (decided by the user) transmit the signal for adjusting power, but it is not limited thereto.

Furthermore, the adjustment signal S3 adjusts the operation frequency of the power amplifier 131 to accordingly adjust the output power of the power amplifier 131 for restricting the power value within the designate power range. In the embodiment, the designate power range is between 0.5 W and 2 W. If the power value of the implantable medical device 2 is not within the designate power range, for example the power value is greater than the upper bound of the designate power range, the user may use the human-computer interface 12 to give an instruction to the first controller 11 so the first controller 11 accordingly issues a power reduction signal to the power amplifier 131 as such operates at a frequency away from the resonant frequency. Otherwise, if the power value is smaller than the lower bound of the designate power range, an instruction is given to the first controller 11 to issue a power increase signal to the power amplifier 131 as such operates at a frequency closer to the resonant frequency.

The second detector 22 of the implantable medical device 2 may immediately detect the power value outputted by the power receiving unit 23, and report the detected status to the external control device 1 by wireless transmission. Thus, the external control device 1 can timely adjust the output power of the power amplifier 131. The implantable medical device 2, when wirelessly powered, is not greatly affected by the depth or alignment of implantation. A desired treatment effect is as such achieved, in addition to convenient user operation.

In the embodiment, the external control device 1 further includes a first detector 16 for detecting the temperature and power dissipation of the power transmitting unit 13. For example, before step S11, the first detector 16 calculates the supplied voltage and the power dissipation of the supplied current of the power amplifier 131, and produces a second detection signal S4 to the first controller 11 for restricting the maximum power of the power amplifier 131. Besides, the temperature of the power amplifier 131 is detected by the first detector 16 to monitor whether the temperature keeps below their pre-determined value. If the power dissipation or the temperature of the power amplifier 131 is beyond their pre-determined value, the power amplifier 131 is considered to be in an abnormal state and the first controller 11 accordingly turns off the power amplifier 131 and stops the first coil operating. If the power dissipation or the temperature of the power amplifier 131 is below their pre-determined value, the power amplifier 131 is considered to be in a normal state and then step S11 of the method for monitoring power supply is entered.

As shown in FIG. 2, in the embodiment, the implantable medical device 2 further includes a sensing unit 24 and a function circuit 26 respectively coupled to the second controller 21. The sensing unit 24 is adapted to sense the temperature value of the implantable medical device 2. For example, it senses the temperature value of the power receiving unit 23 to detect whether the temperature of the power receiving unit 23 is higher than a designate temperature, and transmits a sensing signal S5 to the second controller 21 according to the sensed result. Then, the second controller 21 directs the second signal transceiver unit 25 to transmit a second status information to the first signal transceiver unit 15 of the external control device 1, so the first controller 11 displays the temperature value on the human-computer interface 12 according to the second status information.

For example, the designate temperature may be human body temperature (for example 36° C.) or slightly higher than human body temperature (for example 38° C.). If higher than the designate temperature, the first controller 11 stop the external control device 1 supplying power.

Besides, according to the operation signal outputted from the second controller 21, the function circuit 26 produces the electrical stimulation signal S6 to the organism for electrical stimulation. The operation signal includes treatment time or treatment period of electrical stimulation, frequency of electrical stimulation, or voltage of electrical stimulation, etc. In addition to the electrical stimulation for treatment, the function circuit 26 also transmits its operated treatment data to the second controller 21. Then, the second controller 21 directs the second signal transceiver unit 25 to transmit a third status information to the first signal transceiver unit 15 of the external control device 1 so that the first controller 11 displays the treatment data on the human-computer interface 12 according to the third status information.

The treatment data is not limited, and it may depend on the kind and the application field of the implantable medical device 2. For example, if the implantable medical device 2 is a nerve stimulation device, the treatment data may include values relevant to neural impedance, migration, or open circuit detection, etc. If the implantable medical device is an artificial pacemaker, the treatment data includes relevant values for detecting arrhythmia or VT/VF.

As mentioned above, by the human-computer interface 12, the first status information, the second status information and/or the third status information can be viewed. Furthermore, from the above information, the power detected by the second detector 22, the temperature value sensed by the sensing unit 24, and the treatment data returned by the function circuit 26 are respectively known. Thus, the effect and safety of the implantable medical device 2 during electrical stimulation treatment is improved.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A method for monitoring power supply to an implantable medical device interacting with an external control device, wherein the external control device includes a human-computer interface, a first controller and a power transmitting unit, the implantable medical device includes a power receiving unit, a second controller, a second detector, and a sensing unit electrically connected to the second controller, the method comprising:
   producing a first magnetic field by the power transmitting unit;
   sensing the first magnetic field to produce a second magnetic field and converting the second magnetic field into a direct current by the power receiving unit;
   detecting a power value of the direct current by the second detector to output a first detection signal to the second controller;
   outputting a first status information to the external control device by the second controller according to the first detection signal;
   receiving the first status information by the first controller;
   sensing a temperature value of the implantable medical device b the sensing unit to output a sensing signal to the second controller; and
   outputting a second status information to the external control device by the second controller according to the sensing signal,
   wherein the first controller transmits an adjustment signal to the power transmitting unit if informed of the first status information that the power value is not within a designate power range.

2. The method according to claim 1, wherein the first controller directs the power transmitting unit to produce the first magnetic field according to a parameter indication signal inputted from the human-computer interface.

3. The method according to claim 1, wherein the designate power range is between 0.5 W and 2 W.

4. The method according to claim 1, wherein after received by the first controller, the first status information is displayed on the human-computer interface.

5. The method according to claim 4, wherein if informed of the first status information that the power value is not within the designate power range, the first controller is instructed from the user input on the human-computer interface to transmit the adjustment signal to the power transmitting unit.

6. The method according to claim 5, wherein the designate power range is between 0.5 W and 2 W.

7. The method according to claim 5, wherein the adjustment signal is adapted to adjust the output power of the power transmitting unit for restricting the power value within the designate power range.

8. The method according to claim 5, wherein the designate power range is between 0.5 W and 2 W.

9. The method according to claim 1, further comprising:
   detecting the temperature and the power dissipation of the power transmitting unit by a first detector of the external control device.

10. The method according to claim 1, further comprising:
    displaying the temperature value on the human-computer interface by the first controller according to the second status information.

11. The method according to claim 1, wherein the implantable medical device further comprises a function circuit electrically connected to the second controller.

12. The method according to claim 11, further comprising:
    transmitting an operated treatment data to the second controller by the function circuit;
    outputting a third status information to the external control device by the second controller according to the treatment data; and
    displaying the treatment data on the human-computer interface by the first controller according to the third status information.

13. The method according to claim 1, wherein the external control device and the implantable medical device respectively further comprises a first signal transceiver unit and a second signal transceiver unit, the second controller outputs the first status information to the first signal transceiver unit by the second signal transceiver unit.

* * * * *